United States Patent
Wang et al.

(10) Patent No.: US 10,478,468 B2
(45) Date of Patent: Nov. 19, 2019

(54) METHOD FOR ENHANCING EFFECT OF IMMUNOTHERAPY FOR CANCER

(71) Applicant: PHYTOHEALTH CORPORATION, Taipei (TW)

(72) Inventors: Liang-Shun Wang, New Taipei (TW); Chi-Tai Yeh, Taipei (TW); Chun-Hung Wu, Taipei (TW); Yi-Li Lee, Taipei (TW)

(73) Assignee: PHYTOHEALTH CORPORATION, Taipei (TW)

( * ) Notice: Subject to any disclaimer, the term of this patent is extended or adjusted under 35 U.S.C. 154(b) by 0 days.

(21) Appl. No.: 15/808,534

(22) Filed: Nov. 9, 2017

(65) Prior Publication Data

US 2018/0125912 A1    May 10, 2018

Related U.S. Application Data

(60) Provisional application No. 62/420,087, filed on Nov. 10, 2016.

(51) Int. Cl.
*A61K 36/00* (2006.01)
*A61K 36/481* (2006.01)
*A61K 45/06* (2006.01)

(52) U.S. Cl.
CPC ............ *A61K 36/481* (2013.01); *A61K 45/06* (2013.01)

(58) Field of Classification Search
None
See application file for complete search history.

(56) References Cited

PUBLICATIONS

Wu et al., Inhibition of Astragalus membranaceus polysaccharides against liver cancer cell HepG2. African Journal of Microbiology Research (2010), vol. 4, No. 20, pp. 2181-2183 (Year: 2010).*
Li et al., Selenium-dependent antitumor immunomodulating activity of polysaccharides from roots of A. membranaceus. International journal of biological macromolecules, (Aug. 2014) vol. 69, pp. 64-72 (Year: 2014).*

* cited by examiner

*Primary Examiner* — Qiuwen Mi
(74) *Attorney, Agent, or Firm* — Birch, Stewart, Kolasch & Birch, LLP

(57) ABSTRACT

Disclosed is a method for enhancing the effect of an immunotherapy for cancer in a subject, comprising administering to the subject an effective amount of a polysaccharide extract of *Astragalus membranaceus*. Also disclosed is a method for increasing a subject's pool of M1 macrophages, wherein the subject is suffering from one or more conditions associated with undesirable M2 macrophage activation, the method comprising administering to the subject an effective amount of a polysaccharide extract of *Astragalus membranaceus*.

4 Claims, 7 Drawing Sheets

METHOD FOR ENHANCING EFFECT OF IMMUNOTHERAPY FOR CANCER

CROSS REFERENCE TO RELATED APPLICATION

This non-provisional application claims the benefit under 35 U.S.C. § 119(e) to U.S. Provisional Application No. 62/420,087 filed on Nov. 10, 2016, which is hereby expressly incorporated by reference into the present application.

FIELD OF THE INVENTION

The present invention pertains to a method for enhancing the effect of an immunotherapy for cancer. The present invention also relates to a method for increasing a subject's pool of M1 macrophages and/or enhancing a subject's functional maturation of dendritic cells.

BACKGROUND OF THE INVENTION

Recent studies indicate the critical role of tumor associated macrophages (TAMs), tumor associated dendritic cells (TADCs), cytotoxic T lymphocytes (CTL), and other immunocytes in tumorigenesis and tumor progression. These cells can have a significant impact on the tumor microenvironment (TME) via their cell-to-cell direct effects, or indirect effects by production of cytokines and chemokines. Additionally, products secreted from all these cells have defined specific roles in regulating tumor cell proliferation, angiogenesis, and metastasis. They act in a protumorous capacity in vivo as evidenced by the recent studies indicating that dendritic cells, macrophages, T cells, and neutrophils may be manipulated to exhibit cytotoxic activity against tumors. Therefore, therapy targeting these cells may be promising, or they may constitute drug or anticancer particles delivery systems to the tumors (Cancer immunotherapy: Multi-pronged tumour attack. Nature 28 Vol. 538, 431, 2016).

As a nature's adjuvant and professional antigen-presenting cells (APCs), dendritic cells (DCs) play a central role of immune system ability to react against cancer cells. The principle of DC therapy is to exploit basic ability of DCs to stimulate T cell-based anticancer response. The most important process is the ability of DCs to cross-present antigens with immunostimulatory potential, which relies on presentation of exogenous antigens (normally presented on MHC class II) via MHC class I, enabling direct CD8+ T cell stimulation for anti-tumor immune responses (Cancer immunotherapy via dendritic cells, Nature Reviews Cancer Vol. 12, 265-277, 2012). Most of the therapeutic protocols use monocyte-derived DCs (moDCs), which require their differentiation into immature DCs and subsequent maturation to DCs with anti-tumor function. It should be mentioned that not all mature (or activated) DCs are equivalently immunogenic with anti-tumor function. The biomarkers of functional maturation of DCs with anti-tumor immune response are CD80, CD83, CD86, CD103. The choice of differentiation protocols is absolutely crucial for maximizing immunostimulatory potential of monocyte-derived DCs (moDCs). Most of the protocols use IL-4 and GM-CSF. However, this classical method can be improved as shown by replacement of IL-4 with IL-15 or IFNα.

Tumor associated macrophages (TAMs) are the major players in the tumor microenvironment, and high TAM presented in tumors is associated with a poor prognosis for cancer patients. Based on biological functions, macrophages are divided broadly into two phenotypes: classical M1 and alternative M2 macrophages. The M1 macrophages are driven by the Th1 cytokine interferon-γ, bacterial moieties, and Toll-like receptor (TLR) agonists, and characterized by the production of pro-inflammatory factors such as IL-6, IL-12, IL-23, and tumor necrosis factor-α (TNF-α). Thus, M1 macrophages are involved in the inflammatory response and antitumor immunity. Conversely, the M2 macrophages are associated with Th2 cytokines (IL-4, IL-10, IL-13), and related to an anti-inflammatory response, wound healing, and pro-tumorigenic properties. In general, TAMs resemble the M2 macrophages and M2-like TAMs are critical modulators of the tumor microenvironment for tumor progression (including tumor proliferation, angiogenesis/vasculogenesis, metastasis, and evasion and subversion of host immunosurveillance) and therapeutic resistance (Diverse macrophages polarization in tumor microenvironment. Archives of Pharmacal Research, pp 1-9, 2016). Thus, in addition to be a potentially useful prognostic marker of clinical outcomes, reprogramming of the TAMs from M2 phenotype to M1 phenotype is an important issue in anti-tumor immunotherapy and inhibition of tumor progression.

U.S. Pat. No. 8,728,543 discloses a method of treating idiopathic thrombocytopenic purpura in a human in need thereof, comprising administering a therapeutically effective amount of an extract of *Astragalus membranaceus* to said human.

U.S. Pat. No. 9,139,652 teaches a method for increasing a patient's pool of M1 macrophages, wherein said method comprises administering to the patient a monoclonal antibody, capable of binding to colony-stimulating factor-1 receptor, in an amount effective to increase the patient's pool of M1 macrophages.

BRIEF SUMMARY OF THE INVENTION

According to the present invention, it was unexpectedly found that a polysaccharide extract of *Astragalus membranaceus* is effective in enhancing a functional maturation of dendritic cells and/or repolarizing macrophages towards M1 in a subject.

Accordingly, in one aspect, the present invention provides a method for enhancing the effect of an immunotherapy for cancer in a subject, comprising administering to the subject an effective amount of a polysaccharide extract of *Astragalus membranaceus*.

In some preferred embodiments of the present invention, the polysaccharide extract comprises: an arabinose:galactose ratio ranging from about 1.5:1 to about 3:1; from about 5% to about 15% arabinose; less than about 1.5% rhamnose; from about 3% to about 7% galactose; less than about 4% galacturonic acid; and, from about 70% to about 90% glucose. In one embodiment, the polysaccharide extract has an average molecular weight ranging from about 20 kDa to about 60 kDa.

According to the present invention, the polysaccharide extract may be administered in an amount effective to enhance a functional maturation of dendritic cells and/or repolarize macrophages towards M1 in the subject.

In another aspect, the present invention provides a method for increasing a subject's pool of M1 macrophages, wherein the subject is suffering from one or more conditions associated with undesirable M2 macrophage activation, the method comprising administering to the subject an effective amount of a polysaccharide extract of *Astragalus membranaceus*.

In certain embodiments of the present invention, the one or more conditions associated with undesirable M2 activation comprise cancer, asthma, allergy, or a progressive fibrosis disease.

According to certain embodiments of the present invention, the polysaccharide extract has an average molecular weight ranging from about 20 kDa to about 60 kDa.

According to certain embodiments of the present invention, the method reduces at least one of the following: (i) a macrophage pro-tumoral function; (ii) tumor-associated macrophage recruitment into tumor; (iii) tumor invasion and metastasis; (iv) tumor angiogenesis; (v) tumor growth; and (vi) tumor cell proliferation.

In a further aspect, the present invention provides a method for treating colon cancer in a subject in need thereof, comprising administering to the subject a therapeutically effective amount of a polysaccharide extract of *Astragalus membranaceus*.

According to the present invention, the polysaccharide extract may be administered in an amount effective to enhance a functional maturation of dendritic cells and/or repolarize macrophages towards M1 in the subject.

It is to be understood that both the foregoing general description and the following detailed description are exemplary and explanatory only and are not restrictive of the invention.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred.

In the drawings.

DETAILED DESCRIPTION OF THE INVENTION

Figure 1A:
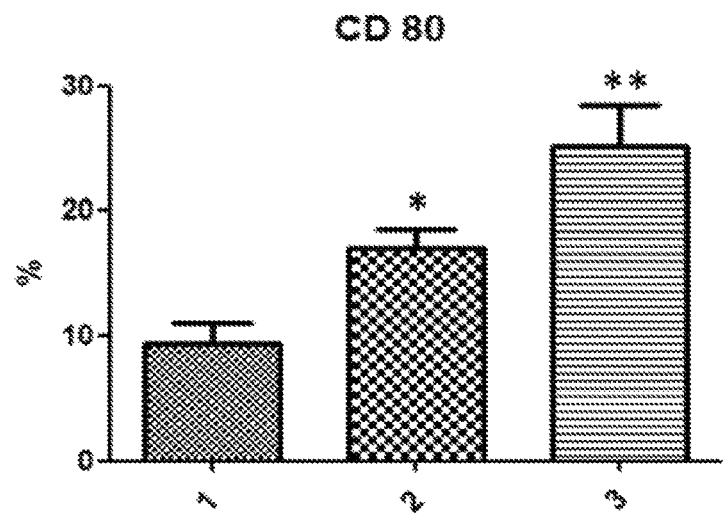
FIG. 1A shows that polysaccharide extract of *Astragalus membranaceus* (PG2) increases the population of CD80+ dendritic cells derived from peripheral blood mononuclear cells (PBMCs) of cancer patients. 1: GM-CSF+IL4; 2: GM-CSF+IL4, followed by the treatment of PG2 (16 mg/ml); 3: GM-CSF+IL4, washed out, and followed by the treatment of PG2 (16 mg/ml). *, $p<0.05$, compared to group 1. **, $p<0.01$, compared to group 1.

In one aspect, the present invention provides a method for enhancing the effect of an immunotherapy for cancer in a subject. The method comprises administering to the subject an effective amount of a polysaccharide extract of *Astragalus membranaceus* (Huang-Chi).

According to certain embodiments of the present invention, the polysaccharide extract has an average molecular weight ranging from about 20 kDa to about 60 kDa.

In some preferred embodiments of the present invention, the polysaccharide extract comprises: an arabinose:galactose ratio ranging from about 1.5:1 to about 3:1; from about 5% to about 15% arabinose; less than about 1.5% rhamnose;

from about 3% to about 7% galactose; less than about 4% galacturonic acid; and, from about 70% to about 90% glucose. In one embodiment, the polysaccharide extract has an average molecular weight ranging from about 20 kDa to about 60 kDa.

The polysaccharide extract of *Astragalus membranaceus* may be prepared by methods known in the art, for example, the methods described in U.S. Pat. No. 8,728,543. According to preferred embodiments of the present invention, the polysaccharide extract of *Astragalus membranaceus* is PG2 (Phytohealth Corporation, Taiwan) (see Hou et al., Mediators of Inflammation, vol. 2015, Article ID 826319, 10 pages, 2015; and Chao et al., J Ethnopharmacol 207, 184-191, 2017).

According to the present invention, the polysaccharide extract may be administered in an amount effective to enhance a functional maturation of dendritic cells and/or repolarize macrophages towards M1 in the subject (or increase the subject's pool of M1 macrophages).

In another aspect, the present invention provides a method for increasing a subject's pool of M1 macrophages, wherein the subject is suffering from one or more conditions associated with undesirable M2 macrophage activation. The method comprises the step of administering to the subject an effective amount of a polysaccharide extract of *Astragalus membranaceus*.

In certain embodiments of the present invention, the one or more conditions associated with undesirable M2 activation comprise cancer, asthma, allergy, or a progressive fibrosis disease.

According to certain embodiments of the present invention, the polysaccharide extract has an average molecular weight ranging from about 20 kDa to about 60 kDa.

In some preferred embodiments of the present invention, the polysaccharide extract comprises: an arabinose:galactose ratio ranging from about 1.5:1 to about 3:1; from about 5% to about 15% arabinose; less than about 1.5% rhamnose; from about 3% to about 7% galactose; less than about 4% galacturonic acid; and, from about 70% to about 90% glucose. In one embodiment, the polysaccharide extract has an average molecular weight ranging from about 20 kDa to about 60 kDa.

According to certain embodiments of the present invention, the method reduces at least one of the following: (i) at least one macrophage pro-tumoral function; (ii) tumor-associated macrophage recruitment into tumor; (iii) tumor invasion and metastasis; (iv) tumor angiogenesis; (v) tumor growth; and (vi) tumor cell proliferation.

In a further aspect, the present invention provides a method for treating colon cancer in a subject in need thereof, wherein the method comprises administering to the subject a therapeutically effective amount of a polysaccharide extract of *Astragalus membranaceus*.

According to certain embodiments of the present invention, the polysaccharide extract has an average molecular weight ranging from about 20 kDa to about 60 kDa.

In some preferred embodiments of the present invention, the polysaccharide extract comprises: an arabinose:galactose ratio ranging from about 1.5:1 to about 3:1; from about 5% to about 15% arabinose; less than about 1.5% rhamnose; from about 3% to about 7% galactose; less than about 4% galacturonic acid; and, from about 70% to about 90% glucose. In one embodiment, the polysaccharide extract has an average molecular weight ranging from about 20 kDa to about 60 kDa.

According to the present invention, the polysaccharide extract may be administered in an amount effective to enhance a functional maturation of dendritic cells and/or repolarize macrophages towards M1 in the subject.

The present invention is further illustrated by the following examples, which are provided for the purpose of demonstration rather than limitation.

EXAMPLES

Example 1: Effects of Polysaccharide Extract of *Astragalus membranaceus* on Dendritic Cell Functional Maturation Polysaccharide extract of *Astragalus membranaceus* PG2 was purchased from Phytohealth Corporation (Taiwan) (see Hou et al., Mediators of Inflammation, vol. 2015, Article ID 826319, 10 pages, 2015; and Chao et al., J Ethnopharmacol 207, 184-191, 2017). Samples of peripheral blood mononuclear cells (PBMCs) were collected from 11 cancer patients. PBMCs ($1 \times 10^6$) were cultured for 2 days and then treated with (1) 20 ng/mL granulocyte-macrophage colony-stimulating factor (GM-CSF) and 20 ng/mL interleukin-4 (IL-4); (2) 20 ng/mL granulocyte-macrophage colony-stimulating factor (GM-CSF) and 20 ng/mL interleukin-4 (IL-4), followed by PG2 (16 mg/ml) for 48 hrs; or (3) 20 ng/mL granulocyte-macrophage colony-stimulating factor (GM-CSF) and 20 ng/mL interleukin-4 (IL-4), washed out, and followed by the treatment of PG2 (16 mg/ml) for 48 hours.

Figure 1B:
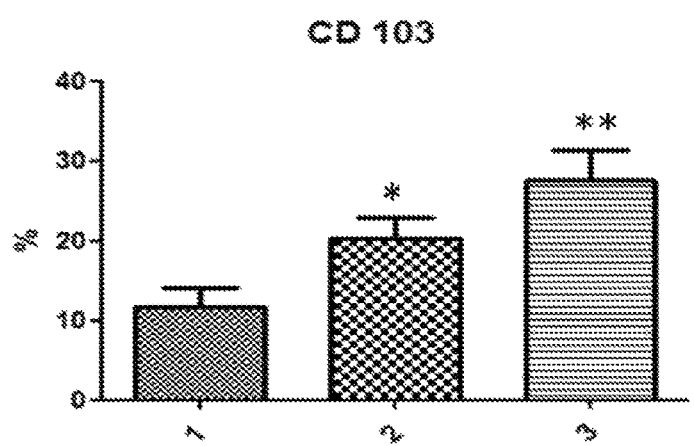
FIG. 1B shows that polysaccharide extract of *Astragalus membranaceus* (PG2) increases the population of CD103+ dendritic cells derived from PBMCs of cancer patients. 1: GM-CSF+IL4; 2: GM-CSF+IL4, followed by the treatment of PG2 (16 mg/ml); 3: GM-CSF+IL4, washed out, and followed by the treatment of PG2 (16 mg/ml). *, $p<0.05$, compared to group 1. **, $p<0.01$, compared to group 1.
Figure 1C:
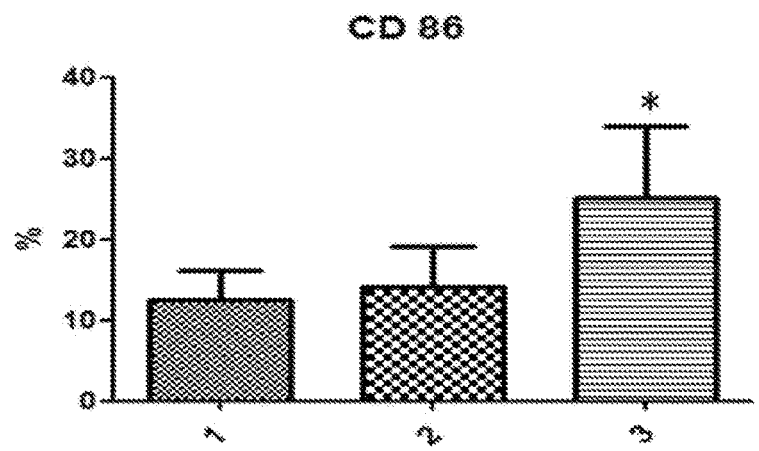
FIG. 1C shows that polysaccharide extract of *Astragalus membranaceus* (PG2) increases the population of CD86+ dendritic cells derived from PBMCs of cancer patients. 1: GM-CSF+IL4; 2: GM-CSF+IL4, followed by the treatment of PG2 (16 mg/ml); 3: GM-CSF+IL4, washed out, and followed by the treatment of PG2 (16 mg/ml). *, $p<0.05$, compared to group 1.
Figure 2A:
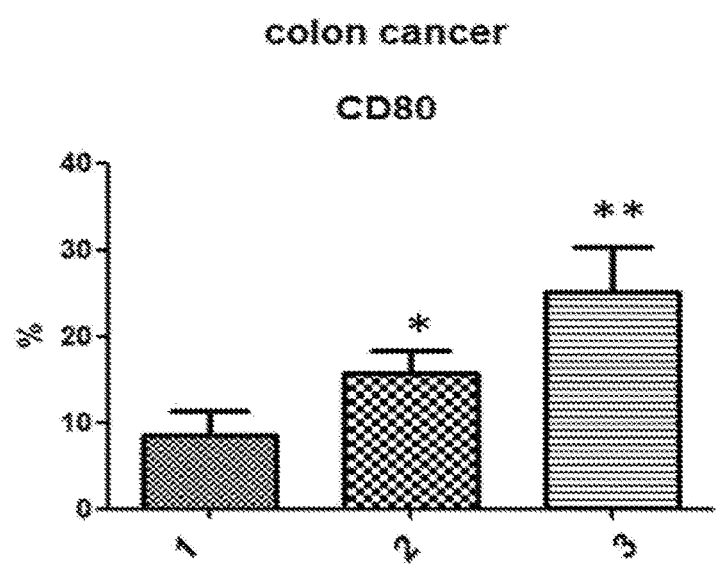
FIG. 2A shows that polysaccharide extract of *Astragalus membranaceus* (PG2) increases the population of CD80+ dendritic cells derived from PBMCs of colon cancer patients. 1: GM-CSF+IL4; 2: GM-CSF+IL4, followed by the treatment of PG2 (16 mg/ml); 3: GM-CSF+IL4, washed out, and followed by the treatment of PG2 (16 mg/ml). *, $p<0.05$, compared to group 1. **, $p<0.01$, compared to group 1.
Figure 2B:
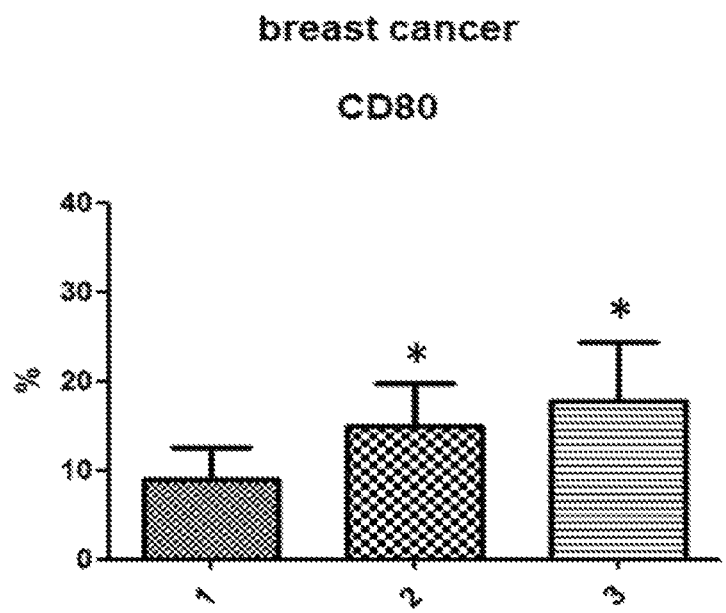
FIG. 2B shows that polysaccharide extract of *Astragalus membranaceus* (PG2) increases the population of CD80+ dendritic cells derived from PBMCs of breast cancer patients. 1: GM-CSF+IL4; 2: GM-CSF+IL4, followed by the treatment of PG2 (16 mg/ml); 3: GM-CSF+IL4, washed out, and followed by the treatment of PG2 (16 mg/ml). *, $p<0.05$, compared to group 1.
Figure 2C:
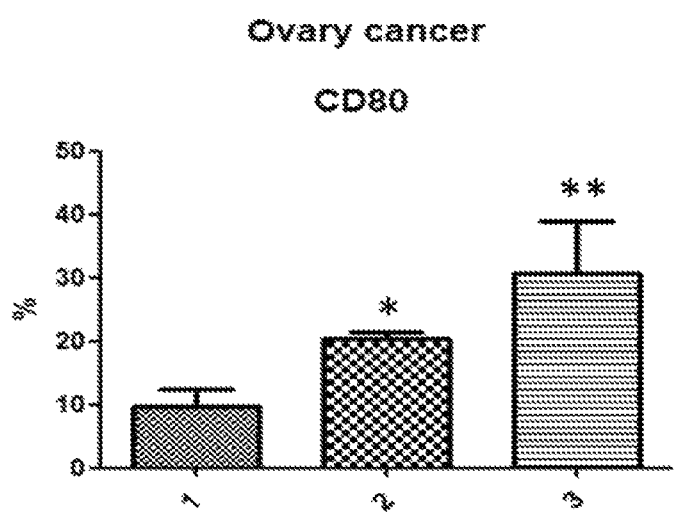
FIG. 2C shows that polysaccharide extract of *Astragalus membranaceus* (PG2) increases the population of CD80+ dendritic cells derived from PBMCs of ovary cancer patients. 1: GM-CSF+IL4; 2: GM-CSF+IL4, followed by the treatment of PG2 (16 mg/ml); 3: GM-CSF+IL4, washed out, and followed by the treatment of PG2 (16 mg/ml). *, $p<0.05$, compared to group 1. **, $p<0.01$, compared to group 1.
Figure 2D:
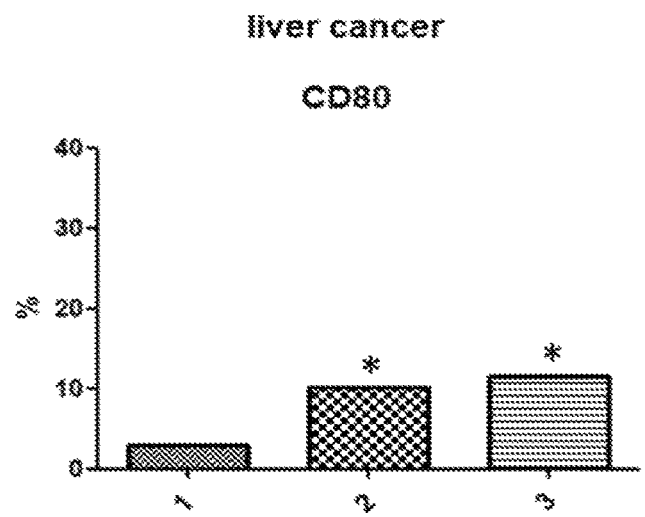
FIG. 2D shows that polysaccharide extract of *Astragalus membranaceus* (PG2) increases the population of CD80+ dendritic cells derived from PBMCs of a liver cancer patient. 1: GM-CSF+IL4; 2: GM-CSF+IL4, followed by the treatment of PG2 (16 mg/ml); 3: GM-CSF+IL4, washed out, and followed by the treatment of PG2 (16 mg/ml). *, $p<0.05$, compared to group 1.

Percentage of CD80+, CD103+, or CD86+ dendritic cells was determined by flow cytometry. The results demonstrate that polysaccharide extract of *Astragalus membranaceus* promotes the functional maturation of dendritic cells (FIGS. 1A-1C). FIGS. 2A-2D show that polysaccharide extract of *Astragalus membranaceus* increases the population of CD80+ dendritic cells derived from PBMCs of patients with different types of cancers. This data suggests that PG2 is a potent immune stimulator for cancer patients with compromised immune system.

Figure 3A:
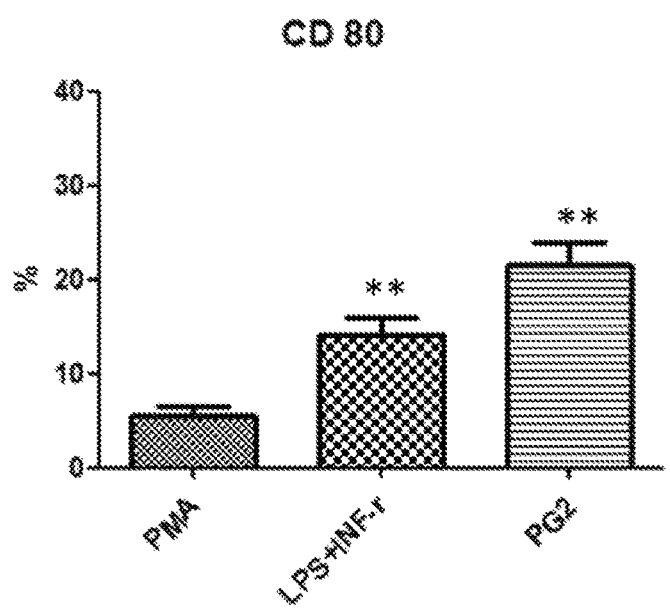
FIG. 3A shows that polysaccharide extract of *Astragalus membranaceus* (PG2) increases the population of CD80+ macrophages derived from PBMCs of cancer patients. **, $p<0.01$, compared to control group (phorbol myristate acetate (PMA) induction only).
Figure 3B:
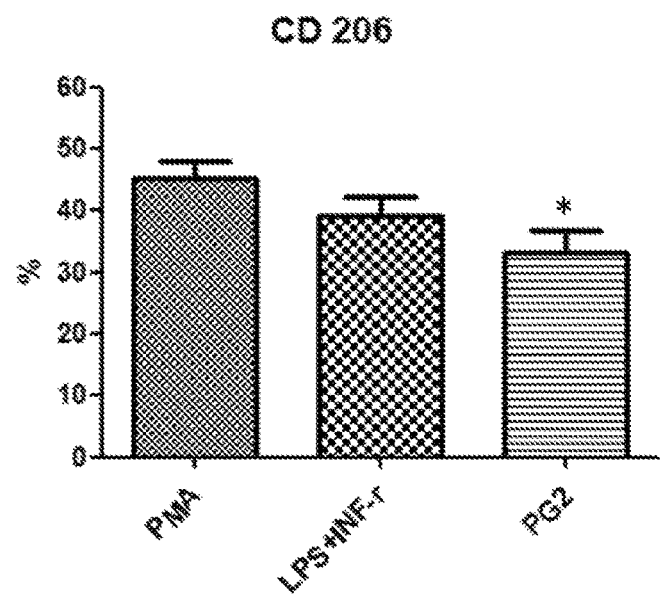
FIG. 3B shows that polysaccharide extract of *Astragalus membranaceus* (PG2) decreases the population of CD206+ macrophages derived from PBMCs of cancer patients. *, $p<0.05$, compared to control group (PMA induction only).
Figure 4A:
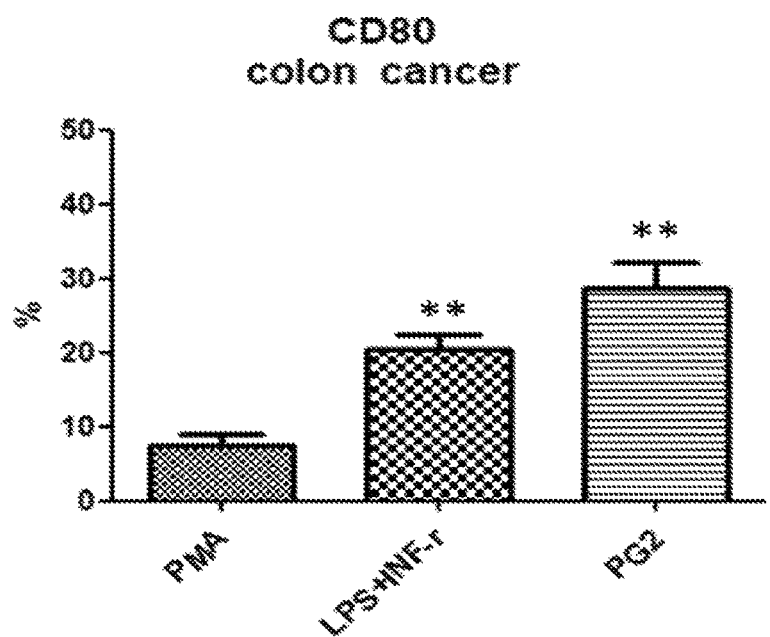
FIG. 4A shows that polysaccharide extract of *Astragalus membranaceus* (PG2) increases the population of CD80+ macrophages derived from PBMCs of colon cancer patients. **, $p<0.01$, compared to control group (PMA induction only).
Figure 4B:
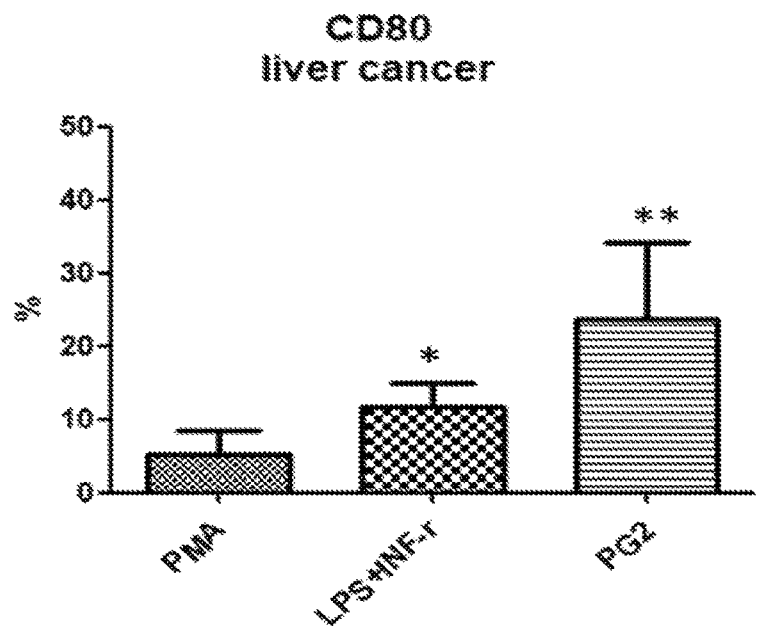
FIG. 4B shows that polysaccharide extract of *Astragalus membranaceus* (PG2) increases the population of CD80+ macrophages derived from PBMCs of liver cancer patients. *, $p<0.05$, **, $p<0.01$, compared to control group (PMA induction only).
Figure 4C:
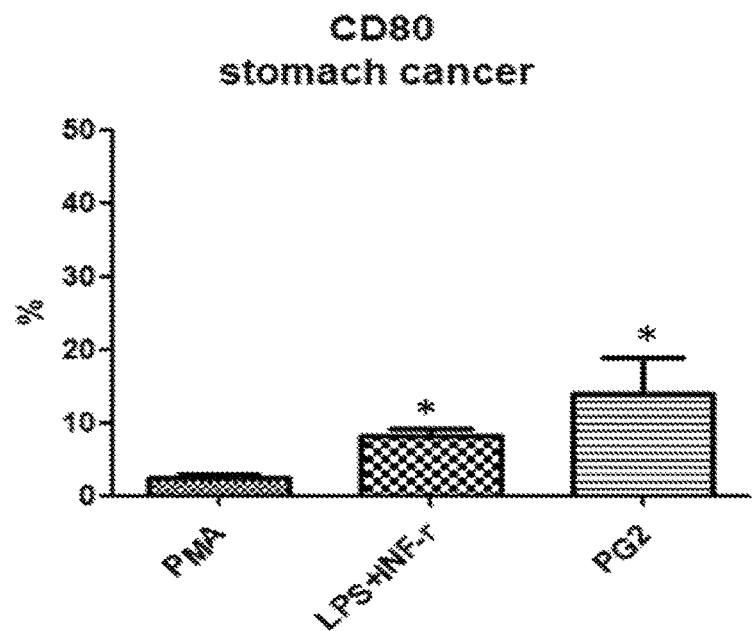
FIG. 4C shows that polysaccharide extract of *Astragalus membranaceus* (PG2) increases the population of CD80+ macrophages derived from PBMCs of stomach cancer patients. *, $p<0.05$, compared to control group (PMA induction only).
Figure 4D:
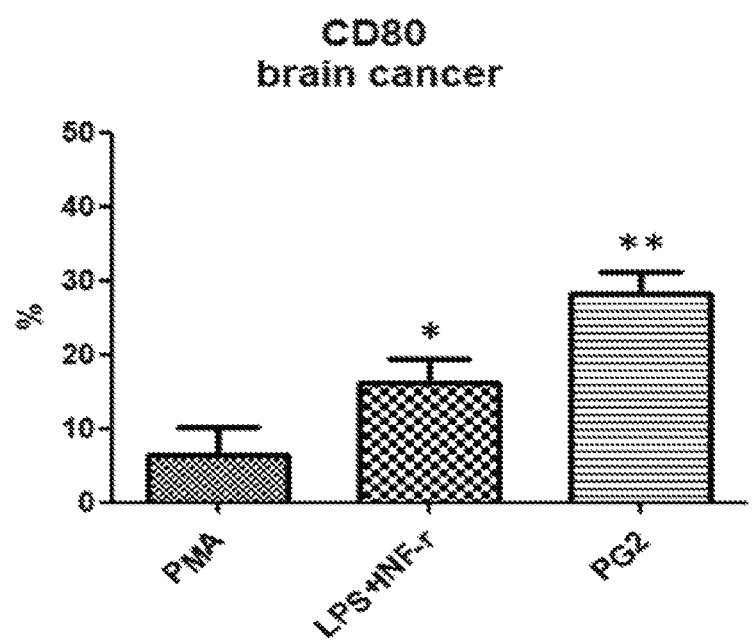
FIG. 4D shows that polysaccharide extract of *Astragalus membranaceus* (PG2) increases the population of CD80+ macrophages derived from PBMCs of brain cancer patients. *, $p<0.05$, **, $p<0.01$, compared to control group (PMA induction only).

Example 2: Effects of Polysaccharide Extract of *Astragalus membranaceus* on Macrophage Phenotype Polysaccharide extract of *Astragalus membranaceus* PG2 was purchased from Phytohealth Corporation (Taiwan). Samples of peripheral blood mononuclear cells (PBMCs) were collected from 17 cancer patients. Seeding PBMCs in culture medium supplemented with 10% FCS at a concentration of $1 \times 10^6$ cells/ml, and transferred in a final volume of 7 ml into 10 ml tissue culture dish. The PBMCs were treated with PMA 25 ng/ml for 24 hours, and further treated with 20 ng/ml IL-4 and IL-13 20 ng/ml for 24 hours. Subsequently, the cells were with PG2 (16 mg/ml) for 48 hours. Percentage of CD80+ or CD206+ macrophages was determined by flow cytometry. The results demonstrate that polysaccharide extract of *Astragalus membranaceus* alters the phenotype of macrophages from M2 to M1 (FIGS. 3A-3B). FIGS. 4A-4D show that polysaccharide extract of *Astragalus membranaceus* increases the population of CD80+ macrophages derived from PBMCs of patients with different types of cancers.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and score of the present invention as defined by the appended claims.

What is claimed is:

1. A method for increasing a subject's pool of M1 macrophages, wherein the subject is suffering from one or more conditions associated with undesirable M2 macrophage activation, the method comprising
administering to the subject an effective amount of a polysaccharide extract of *Astragalus membranaceus*, said polysaccharide extract comprising an arabinose:galactose ratio ranging from about 1.5:1 to about 3:1; from about 5% to about 15% arabinose; less than about 1.5% rhamnose; from about 3% to about 7% galactose; less than about 4% galacturonic acid; and, from about 70% to about 90% glucose.

2. The method of claim 1, wherein the one or more conditions associated with undesirable M2 activation comprise cancer, asthma, allergy, or a progressive fibrosis disease.

3. The method of claim 1, wherein the polysaccharide extract has an average molecular weight ranging from about 20 kDa to about 60 kDa.

4. The method of claim 1, wherein the method reduces at least one of the following: (i) a macrophage pro-tumoral function; (ii) tumor-associated macrophage recruitment into tumor; (iii) tumor invasion and metastasis; (iv) tumor angiogenesis; (v) tumor growth; and (vi) tumor cell proliferation.

* * * * *